United States Patent
Allgood

[19]

[11] Patent Number: 5,907,877
[45] Date of Patent: Jun. 1, 1999

[54] SANITARY DISPOSABLE STIRRUP COVERS

[76] Inventor: Lynn Allgood, 1211 Stillwater Rd., Anniston, Ala. 36207

[21] Appl. No.: 09/144,086

[22] Filed: Aug. 31, 1998

Related U.S. Application Data

[60] Provisional application No. 60/059,101, Sep. 16, 1997.
[51] Int. Cl.[6] .......................... A61G 13/10; A61G 13/12
[52] U.S. Cl. ............................... 5/649; 150/154; 383/43; 383/71
[58] Field of Search .............................. 5/649, 624, 648, 5/650, 651, 658; 297/220, 228.11; 150/160, 155, 154, 156; 383/43, 71

[56] References Cited

U.S. PATENT DOCUMENTS

| | | | |
|---|---|---|---|
| 180,571 | 8/1876 | Gillette | 383/71 |
| 1,696,775 | 12/1928 | Martz | 297/220 |
| 3,426,815 | 2/1969 | Ashlin et al. | 150/160 |
| 3,452,978 | 7/1969 | Creelman | 5/649 |
| 4,046,365 | 9/1977 | Dungan | 5/649 |
| 4,360,193 | 11/1982 | Mitchell | 5/649 |
| 4,407,687 | 10/1983 | Mitchell | 5/649 |
| 5,302,124 | 4/1994 | Lansing et al. | 150/154 |
| 5,535,543 | 7/1996 | Alexander | 383/43 |

FOREIGN PATENT DOCUMENTS

| | | |
|---|---|---|
| 1169159 | 10/1969 | United Kingdom . |
| 2041737 | 9/1980 | United Kingdom . |

*Primary Examiner*—Alex Grosz
*Attorney, Agent, or Firm*—Richard C. Litman

[57] ABSTRACT

A cover for use on a medical examination table stirrup, the cover forming a pocket. The pocket is defined by an upper edge and side edges extending downwardly from the upper edge to a bottom edge, the bottom edge being open to form a mouth. The pocket receives the frame of the stirrup. A closure tie, such as elastic, for securing the pocket about the stirrup frame is provided in the bottom edge.

6 Claims, 2 Drawing Sheets

SANITARY DISPOSABLE STIRRUP COVERS

CROSS-REFERENCE TO RELATED APPLICATION

This application claims the benefit of U.S. Provisional Patent Application Ser. No. 60/059,101, filed Sep. 16, 1997.

BACKGROUND OF THE INVENTION

1. Field of the Invention

The present invention relates to sanitary protective coverings of the type commonly used in physician's offices to provide a clean surface against which the patient's body or portions thereof may rest during examination or treatment. More specifically, the invention refers to a type of disposable cover for use on the conventional stirrups found on certain examination tables.

2. Description of Related Art

Today, certain physicians' examination tables are equipped with a pair of adjustable foot supports or stirrups. These stirrups are especially useful to support the patient's feet and legs in an elevated, separated position so that various examinations and treatments may be performed. Typically, the stirrups are made of metal, and come in direct contact with the patients' feet. Occasionally, the patient may be permitted to keep shoes on during the exam. In either case, the stirrup is subjected to possible contamination by debris, germs and/or organisms on the feet or shoes. Further contamination may occur during the procedures performed. For this reason, there is a need to provide a sanitary cover for the stirrups to protect the current patient from being exposed to possible contaminants left by the previous patient, and simultaneously preventing transfer to subsequent patients and/or health care providers.

Previous attempts have been made to address comfort concerns involved in using stirrups. Metal is a cold and unforgiving material. Patients, often barefoot, express discomfort at placing their feet on the cold surface. In prolonged exams or those where the patient must exert pressure on the stirrup, the unforgiving nature of metal, along with the shape of the stirrup, make for a bothersome experience. To alleviate some of these problems, some physicians have covered the stirrups with common gym socks.

U.S. Pat. No. 4,360,193 which issued on Nov. 23, 1982, to Mitchell for a cover for stirrup of physician's examination table discloses a padded cover that slips over the stirrup and is held in place by a sleeve portion. The cover is provided with a foam padding, especially at the heel portion, for adding comfort. U.S. Pat. No. 4,407,687 which issued to Mitchell on Oct. 4, 1983 discloses a method of manufacturing this cover.

UK Patent Application 2,041,737 published Sep. 17, 1980, for an adjustable labor-delivery-recovery hospital bed includes a pair of padded crutches, for purposes similar to stirrups, without mention of use of disposable sanitary covers.

Other devices have used a padded sleeve-like cover slipped over or around the stirrup secured by a zipper as disclosed by U.S. Pat. No. 3,452,978 (comfort device for foot stirrups of physician's examining table) which issued on Jul. 1, 1969, to Creelman.

U.S. Pat. No. 4,046,365 which issued on Sep. 6, 1977, to Dungan discloses another attempt at adding comfort to examination table stirrups. This example comprises a flat annular blank of padded material such as foam plastic which was secured to the stirrups by several tiedowns.

Covering devices such as that disclosed in U.S. Pat. No. 5,302,124 which issued to Lansing, et al. on Apr. 12, 1994, for disposable protective sleeve for dental apparatus such as light curing guns are known to provide sanitary protection for multi-use equipment. This cover, however, is not adapted to recognize the special concerns of an examining table stirrup.

Other covering devices have been used to protect the item covered are known, but are less related to the present invention or the field of sanitary disposable covers. Among these are British Patent No. 1,169,159 (detachable decorative seat belt cover) published Oct. 29, 1969.

None of the above inventions and patents, taken either singly or in combination, is seen to describe the instant invention as claimed.

SUMMARY OF THE INVENTION

The invention is a disposable sanitary stirrup cover for use on a stirrup of the type found on medical examination tables and the like. The stirrup comprises a central opening surrounded by a frame having top, side, and bottom elements. The cover itself comprises a sheet of material joined to provide a pocket means defined by an upper edge and side edges extending downwardly from the upper edge to a bottom edge. The bottom edge remains open to form a mouth for receiving the frame of the stirrup. At the bottom edge a means for securing said pocket about the stirrup frame, such as elastic, is used.

Accordingly, it is a principal object of the invention to provide a sanitary cover for examination table stirrups.

It is another object of the invention to provide a sanitary cover for examination table stirrups that is disposable.

It is a further object of the invention to provide a sanitary cover for examination table stirrups using elastic as securing means.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
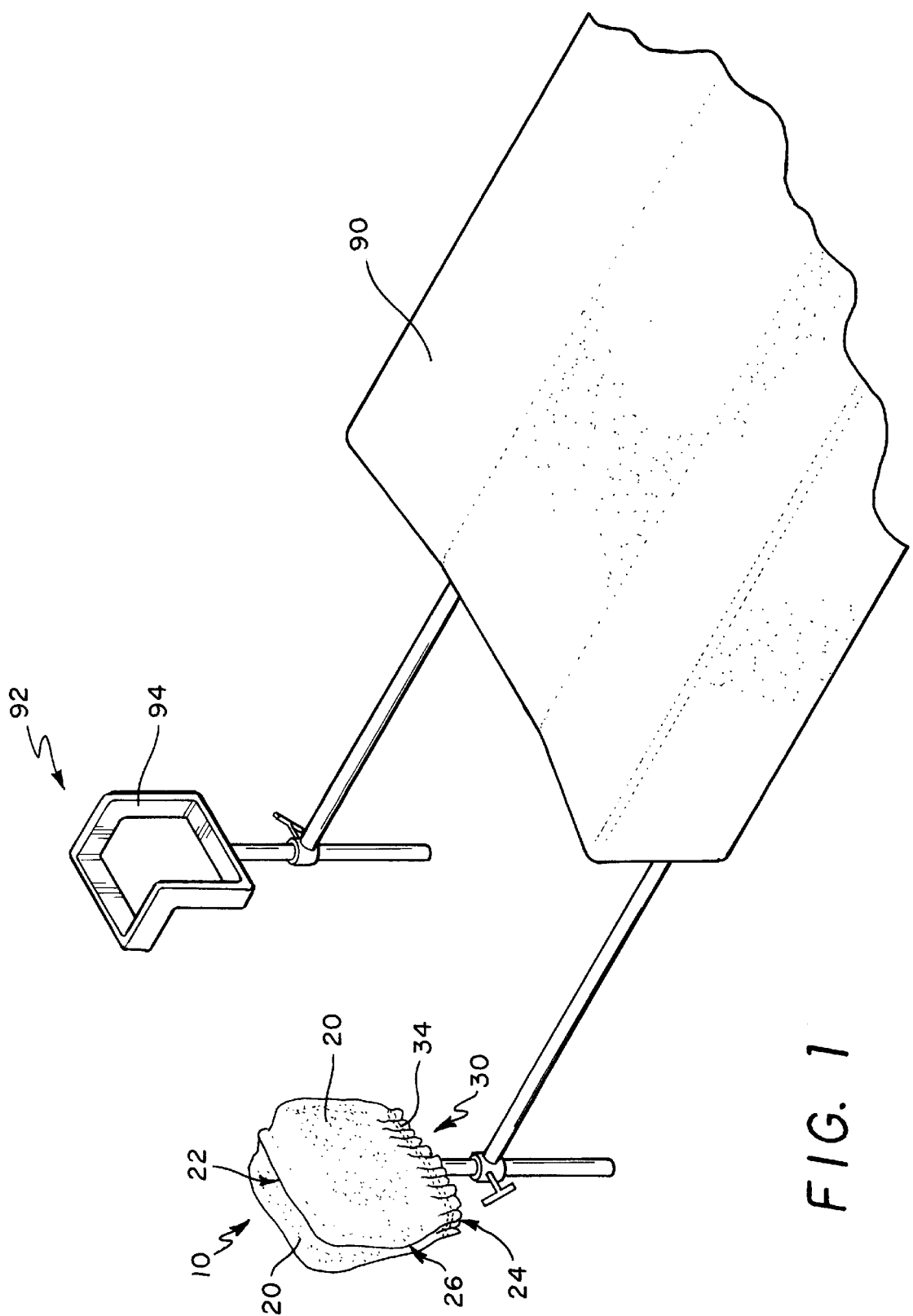
FIG. 1 is an environmental perspective view of a cover in use on a stirrup, and an uncovered stirrup and examination table.
Figure 2:
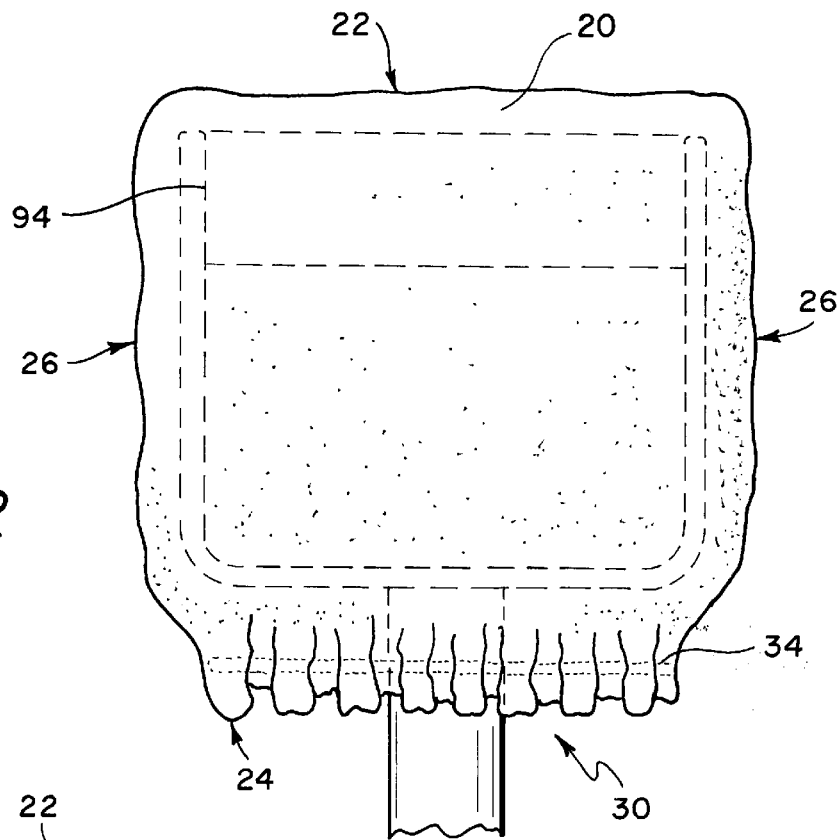
FIG. 2 is a front elevational view of the cover in place over a stirrup.
Figure 3:
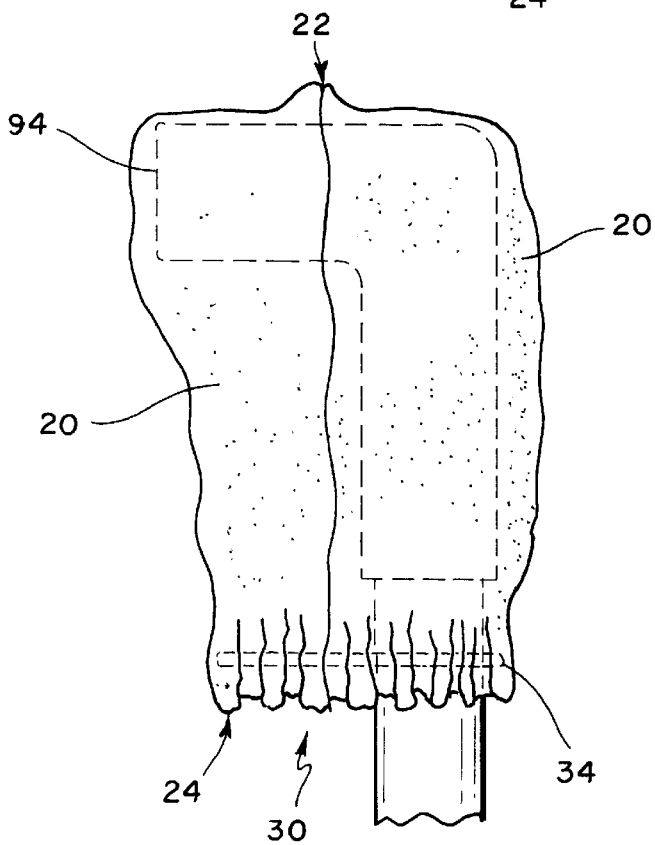
FIG. 3 is a side elevational view of the cover in place over a stirrup.

Referring now to the figures by numerals of reference, the present invention is a disposable sanitary cover 10 for use on a stirrup 92 of the type found on medical examination tables 90 and the like. The stirrup 92 is made up of a frame 94 having top, side, and bottom elements that define a central opening. The cover 10 comprises first and second sheets 20 of inexpensive material, such as disposable paper web, a plastic sheet, a cloth fabric or fleece. The two sheets 20 are roughly equivalent in size, and joined conventionally (e.g., stitching, adhesive, sonic welding, etc.) to provide a pocket therebetween. An upper edge 22 and side edges 26 extending downwardly from the upper edge 22 to a bottom edge 24, define the pocket. Alternatively, a single sheet 20 may be used, with an appropriate fold forming an edge other than the bottom. In either embodiment, three edges must be closed, at least two of them being joined; the third edge may be similarly joined or formed by the fold. The bottom edge 24 must remain open to form a mouth 30 for receiving the stirrup frame 94 into the pocket. A closure loop or tie for securing the pocket about the stirrup frame 94 is provided in the bottom edge 24 of the pocket. Most preferably, elastic band 34 will be used along the bottom edge 26 of the pocket to collapse the mouth 30 about the stirrup frame 94, thereby securing the cover 10 in place.

Optionally, the cover may be made of lightweight foam material, or otherwise be adapted to accept a foam material insert such that comfort as well as protection may be afforded the patient.

Before a patient is asked to use the stirrups, the physician or assistant may simply remove and discard previously used covers, and replace them with a fresh set of covers. The elastic in the bottom edge of the cover allows it to stretch over the stirrup, and yet remain securely in place once in position. Each patient is therefore protected from possible contamination from the previous patient.

It is to be understood that the present invention is not limited to the embodiments described above, but encompasses any and all embodiments within the scope of the following claims.

I claim:

1. An improved cover in combination with a stirrup of the type found on medical examination tables and the like, the stirrup comprising a frame having top, side, and bottom elements which define a central opening, said cover comprising:

a first sheet of inelastic material and a second sheet inelastic of material of substantially equal size;

means for joining said first and second sheets to provide therebetween a pocket means, said pocket means having an upper edge and side edges extending downwardly from said upper edge, and further, a bottom edge, said bottom edge being open to form a mouth, said pocket means thus being dimensioned and configured for receiving the frame of the stirrup; and means for securing said pocket about the stirrup frame comprising an elastic band disposed within said bottom edge of said pocket for collapsing said mouth of said pocket about the stirrup frame.

2. The improved combination as recited in claim 1, wherein said first sheet and said second sheet are made of a disposable paper web.

3. The improved combination as recited in claim 1 wherein said first sheet and said second sheet are made of a disposable fabric.

4. An improved cover in combination with a stirrup of the type found on medical examination tables and the like, the stirrup comprising a frame having top, side, and bottom elements which define a central opening, said cover comprising:

a single sheet of inelastic material;

means for joining said sheet to itself to provide a pocket forming a mouth, said pocket means being dimensioned and configured for receiving the frame of the stirrup; and means for securing said pocket about the stirrup frame comprising an elastic band disposed within a bottom edge of said pocket for collapsing said mouth of said pocket about the stirrup frame.

5. The improved combination as recited in claim 4 wherein said sheet is made of a disposable paper web.

6. The improved combination as recited in claim 4 wherein said sheet is made of a disposable fabric.

* * * * *